United States Patent [19]

Stewart

[11] Patent Number: 4,857,273
[45] Date of Patent: Aug. 15, 1989

[54] BIOSENSORS

[75] Inventor: William J. Stewart, Blakesley, United Kingdom

[73] Assignee: Plessey Overseas Limited, Ilford Essex, United Kingdom

[21] Appl. No.: 848,680

[22] Filed: Apr. 4, 1986

[30] Foreign Application Priority Data

Apr. 12, 1985 [GB] United Kingdom ............... 8509491

[51] Int. Cl.$^4$ ........................................... G01N 21/77
[52] U.S. Cl. .................................... 422/68; 350/96.12; 350/96.15; 350/96.19; 350/96.34; 422/55; 422/57; 422/69; 435/287; 435/291; 435/808; 436/805
[58] Field of Search ................... 436/805; 422/57, 58, 422/69, 68, 55; 350/96.12, 96.15, 96.17, 96.19, 96.34; 435/287, 291, 808

[56] References Cited

U.S. PATENT DOCUMENTS 3,883,221  5/1975  Rigrod ............................... 350/96
4,059,338  11/1977  Hartelius ...................... 350/96.19 X
4,565,422  1/1986  Seymour et al. ................ 350/96.19
4,582,809  4/1986  Block et al. ...................... 422/68 X
4,637,684  1/1987  Tomita et al. ................... 350/96.19
4,653,844  3/1987  Ward ............................. 350/96.19 X

FOREIGN PATENT DOCUMENTS 0075353  3/1983  European Pat. Off. .
1287035  8/1972  United Kingdom .
1409475  10/1975  United Kingdom .
2156970  10/1985  United Kingdom .

OTHER PUBLICATIONS

CRC Handbook of Chemistry and Physics, 64th Edition, CRC Press, Boca Raton, Fla., 1983-1984, p. B-66.
R. M. Sutherland et al., "Detection of Antibody-Antigen Reactions at a glass liquid interface as a Novel Optical Immunoassay Concept". Proceedings of 2nd Optical Fiber Conference (Stuttgart 1984), Paper, No. 28, p. 75.

Primary Examiner—Robert J. Hill, Jr.
Attorney, Agent, or Firm—Fleit, Jacobson, Cohn, Price, Holman & Stern

[57] ABSTRACT

A biosensor includes an optically dense body provided with a coating sensitized to a specific assay species, and an input and output coupling structure. Light signal response is enhanced by incorporating a partially reflecting, partially transmitting medium between the coupling structure and the optically dense body having a lower refractive index. The thickness of such medium is chosen so that light may be coupled by frustrated total internal reflection and to enable the medium to serve as a resonant mirror.

6 Claims, 1 Drawing Sheet

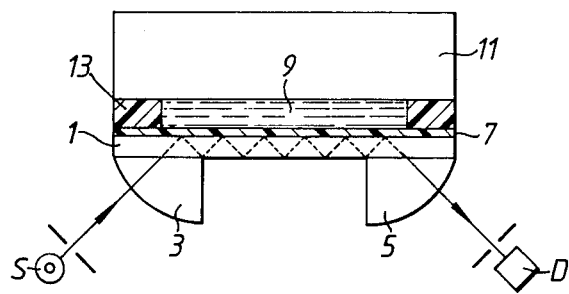
FIG. 1.
PRIOR ART
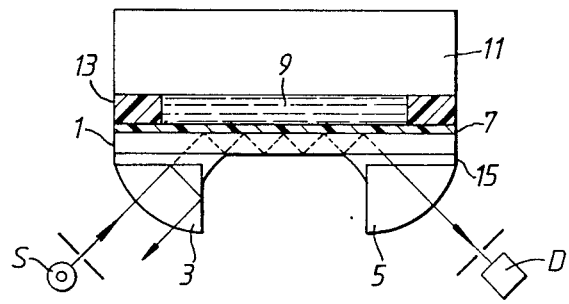
FIG. 2.
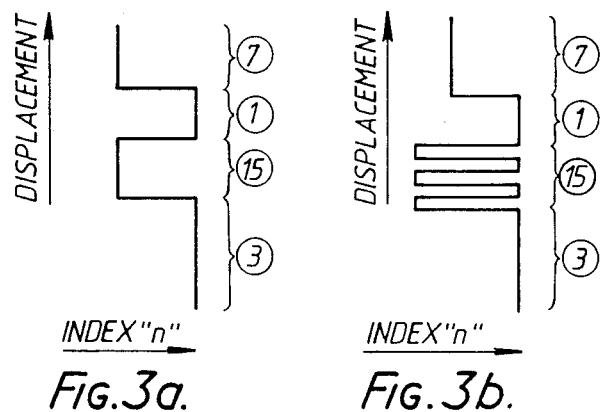
FIG. 3a.    FIG. 3b.

BIOSENSORS

BACKGROUND OF THE INVENTION

1. Field Of The Invention

The present invention concerns biosensers, i.e. sensors for detecting and/or monitoring or quantifying the presence and/or behavior of specific species in test fluid samples. The invention is applicable to the following: immunoassays, i.e.; the detection of antibodies, antigens, or hormones in blood samples; pollution monitoring; and, to the monitoring of clinical diagnostic reactions involving enzymes and the like.

2. Description of Related Art

A recent article entitled "Detection of Antibody—Antigen Reactions at a glass-liquid Interface as a Novel Optical Immunoassay Concept", (1984), R. M. Sutherland et al (Proceedings of 2nd Optical Fibre Conference (Stuttgart 1984) page 75) describes a biosensor in which an antibody species is covalently immobilized onto the surface of a planar or fibre-optic waveguide. The reaction of immobilized antibody with antigen in a sample solution is detected using the evanescent wave component of a light beam which has been totally internally reflected many times within the waveguide. The evanescent wave has a characteristic penetration depth of a fraction of a wavelength into the aqueous phase, thus optically interacting with substances bound to or very close to the interface and only minimally with the bulk solution.

Reference is also made to our United Kingdom Patent Application BG 2156970A published Oct. 16, 1985, which discloses optic-waveguide biosensors and a similar technique. The content of that disclosure is incorporated herein by reference.

SUMMARY OF THE INVENTION

The present invention is intended to enhance biosensor response for a given beam power.

In accordance with the invention there is provided a biosensor comprising:

an aplically dense body having a coating sensitized for a given assay species; and Light coupling means adjacent to the optically dense body, to direct light into and out of the same; wherein a light reflecting and partially transmissive medium is interposed between the aplically dense body and the light coupling means, so that the coating, the optically dense body, and the light reflecting and partially transmitting medium together provide a mirrored resonant cavity.

In the above defined construction the combination of coating, body, and reflecting medium have the propertis of a mirrored resonant cavity. The power of radiation within this cavity is thus enhanced relative to the power of the input beam and the power of the interactive evanescent wave extending into the sensitive coating is likewise enhanced, thereby improving device sensitivity to species absorbed by the coating.

The reflecting partially transmissive medium may be realized by a thin single layer of relatively low refractive index transparent material. Alternatively, it may be realized by a dielectric multilayer structure.

BRIEF DESCRIPTION OF THE DRAWINGS

In the accompanying drawings:

FIG. 1 is an illustrative cross-section view of a known biosensor;

FIG. 2 is an illustrative cross-section view of a biosensor modified in accordance with this invention; and FIG. 3 illustrates schematic refractive index profiles for a modified biosensor incorporating (a) a single layer reflector; and (b) a multi-layer structure reflector, respectively.

DESCRIPTION OF THE PREFERRED EMBODIMENTS

Embodiments of the invention will now be described, by way of example only, with reference to the drawings accompanying this specification.

In FIG. 1 there is shown a known biosensor in which light from a source S is directed into a planar waveguide 1 by means of a first coupling prism 3 and propagated by multiple total internal reflection to exit by means of a second coupling prism 5 where it is directed onto a light detector D. The external surface of the waveguide 1 is provided with a sensitized organic is coating 7. The latter coating exposed to a sample liquid 9 which is contained by means of a flow cell 11 and gasket 13 arrangement. In the coating 7, antibody material is covalently immobilized and this responds to any specific antigen material in the sample liquid to which it is exposed. The waveguide is of fused quartz material and this provides a large differential in optical density between the quartz waveguide 1 (high refractive index $n_1$) and the adjacent coating 7 (low refractive index $n_2$). Light is totally internally reflected within the body of the waveguide 1, with a portion of the optical power, propagating as an evanescent wave in the coating medium 7. The binding of antigen by the immobilized antibody is monitored by a resultant increase in the light absorption measured at the detector D.

In the inventive modification shown FIG. 2, a partially transmissive light reflecting layer 15 of relatively low refractive index material—for example an evaporated or sputtered layer of magnesium fluoride-is interposed between the coupling prisms 3, 5 and the planar waveguide 1. This construction may be used in conjunction with an infra-red light injection laser as light source S—typical light wavelength $0.8\mu$. Similar apparatus may be used for visible light and for ultra-violet light, but in the latter case a layer 15 of alumina or similar material would be used—typical light wavelength 270 nm. Light is coupled to the waveguide 1 by frustrated total internal reflection, and the thickness of the interposed layer 15 is chosen accordingly. The refractive index profile for this assembly of media—coating 7, waveguide 1, reflector 15 and coupling member 3—is shown FIG. 3(a). As can be seen, the waveguide 1 is isolated by media 7, 15 of lower refractive index. Incident light coupled to the waveguide is thus resonantly trapped between the reflecting layer 15 (highly reflecting but partially transmitting) and the coating/waveguide interface 7/1. The power level is high in this region. The light subsequently leaks back into the bulk medium, the second coupling member 5, after which it is monitored by the photodetector D. The evanescent wave in the coating 7 will interact with any adsorbed species in this layer 7 and in turn will modify the absorption and phase shift of the light beam monitored. The latter is enhanced by this resonant effect.

As an alternative modification, the single interposed layer 15 of the assembly shown in FIG. 2 may be replaced by a dielectric multilayer structure 15. Such dielectric multilayer structures are per se well known to persons of oridinary skill in the art and thoroughly understood as to function and use so that the details thereof form no part of the present invention. A typical index profile for this modified assembly is shown in FIG. 3(b). This further modification has the advantage of allowing a relaxation in coupling constraints. As an example, a multilayer structure providing 90% reflection and 10% transmission provides a factor x10 enhancement of power within the resonant cavity.

The present of assay species may be detected and/or monitored by measuring changes in the absorbtion or polarazation of the monitored light beam. The interaction will depend on the frequency and angle of incidence of the light beam. Thus source S and detector D may be singular components mechanically scanned over a range of angles, or may each comprise an extended array, each component being electronically addressed to simulate a scan. Alternatively, the source S and detector D may be set up in an optimal static configuration.

Having described the invention and the manner in which it may be performed, I/We claim:

1. A biosensor comprising: an optically dense body having a coating sensitized for a given assay species, light coupling means positioned in operative adjacent relation to the optically dense body for directing light into and out of the same, and means operatively associated with the light coupling means for esablishing a mirrored resonant cavity within the optically dense body by frustrated total internal reflection, including a light reflecting and partially transmissive medium operatively interposed between the optically dense body and the light coupling means.

2. The biosensor as claimed in claim 1, wherein the light reflecting and partially transmissive medium comprises a single layer of material of a thickness establishing light coupling by frustrated total internal reflection, said material having a refractive index lower than that of the optically dense body.

3. The biosensor as claimed in claim 2, wherein the single of material layer is magnesium fluoride.

4. The biosensor as claimed in claim 2, wherein the single layer of material is alumina.

5. The biosensor as claimed in claim 1, wherein the light reflecting and partially transmissive medium comprises a dielectric multilayer structure.

6. A monitoring system comprising a light source, a photodetector, a biosensor comprising: an optically dense body having a coating sensitized for a given assay species, light coupling means operatively positioned adjacent to the optically dense body for directing light into and out of the same and means operatively associated with the light coupling means for esablishing a mirrored resonant cavity within the optically dense body by frustrated total internal reflection, including a light reflecting and partially transmissive medium operatively interposed between the optically dense body and the light coupling means, said light source and the photodetector being positioned relative to the biosensor in optically coupled resonance relation to each other.

* * * * *